United States Patent [19]

Sawchuk

[11] Patent Number: 5,307,695
[45] Date of Patent: May 3, 1994

[54] WATER SAMPLING UNIT

[75] Inventor: David L. M. Sawchuk, Sarnia, Canada

[73] Assignee: Polysar Rubber Corporation, Sarnia, Canada

[21] Appl. No.: 889,205

[22] Filed: May 27, 1992

[30] Foreign Application Priority Data

Jun. 21, 1991 [CA] Canada ............................ 2045281-1

[51] Int. Cl.$^5$ .............................................. G01N 1/10
[52] U.S. Cl. .................................... 73/864.51; 220/512
[58] Field of Search ........................ 73/863.31, 864.51, 864.61-864.67, 73/864.91; 220/501, 507, 509, 512, 514, 516, 523, 527

[56] References Cited

U.S. PATENT DOCUMENTS

| | | | |
|---|---|---|---|
| 818,190 | 4/1906 | Phillips | 220/509 |
| 1,967,794 | 7/1934 | Wagner | 220/512 |
| 2,292,626 | 8/1942 | Ferguson | 220/507 |
| 4,326,629 | 4/1982 | Tate | 220/516 |
| 4,625,574 | 12/1986 | Robbins | 73/864.91 |
| 4,718,289 | 1/1988 | Barrett | 73/864.51 |
| 4,744,256 | 5/1988 | Nisken | 73/864.66 |
| 4,852,413 | 8/1989 | Nisker et al. | 73/864.67 |

FOREIGN PATENT DOCUMENTS 0564683  10/1944  United Kingdom ............ 73/864.66

Primary Examiner—Robert Raevis
Attorney, Agent, or Firm—Joseph C. Gil; Godfried R. Akorli

[57] ABSTRACT

Water sampling equipment and a method of using the same are provided wherein the water sampling equipment comprises a two component metal containment unit containing glass sample bottles, the two components of which are screwable detachable one from the other and which are designed to provide flow through of water from the water stream to be sampled allowing the glass sample bottles to readily be filled.

4 Claims, 2 Drawing Sheets

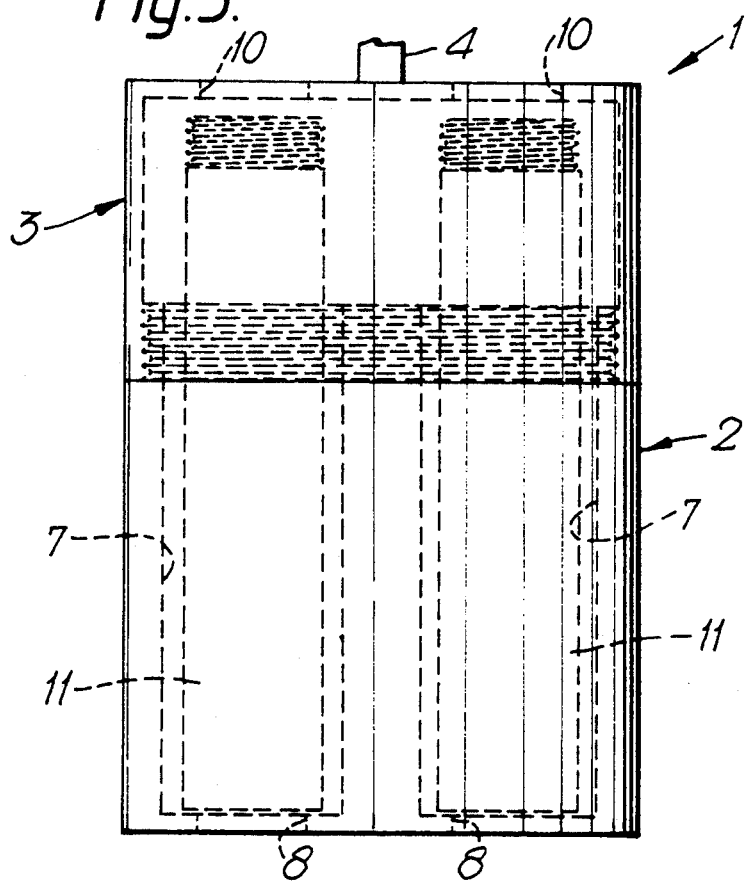
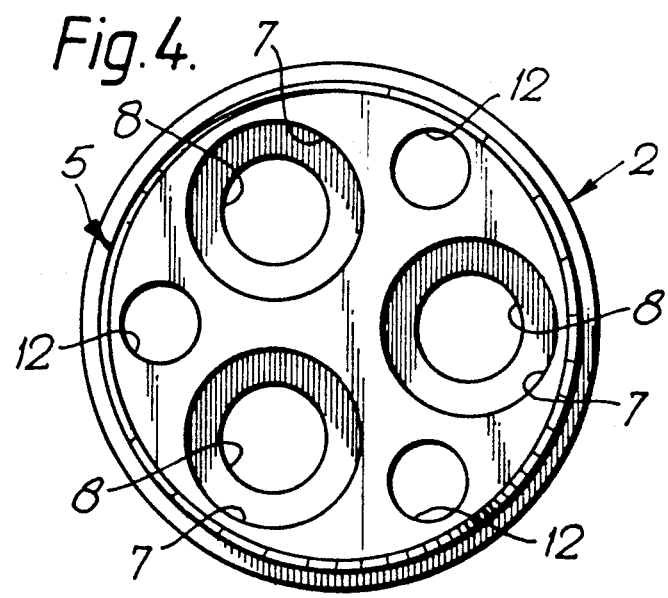

WATER SAMPLING UNIT

FIELD OF THE INVENTION

This invention is directed to equipment for use in collecting water samples and to a method of using such equipment for the collection of samples.

BACKGROUND OF THE INVENTION

The needs for and the rules and regulations applicable to collecting samples of aqueous streams for analysis under various environmental and regulatory items of legislation have evolved over the years. A prominent feature of many of the applicable rules is the obtaining of a typical sample of the aqueous stream in a container which will not contribute to or remove any of the impurities present in the sample. Generally, it is preferred to obtain the sample in a prewashed glass container which creates the problem of how to get the glass container to the appropriate sampling point. The Applicant is not aware of prior art available to the public on this subject and material to the invention defined in this application.

SUMMARY OF THE INVENTION

I have designed equipment for use in collecting water samples for subsequent analysis. The equipment that I have designed comprises a sampling unit which is connected to a sampling line in order that it can be lowered to the desired sample point. The sampling unit contains not less than three volatiles analysis glass sample bottles in which the water sample is collected.

Accordingly, my invention is a sampling unit for collecting water samples for subsequent analysis, wherein said sampling unit comprises a metal containment unit and contained within said containment unit three volatiles analysis glass sample bottles, wherein said metal containment unit comprises a bottom component and a top component, said bottom component comprising a circular cross section rod-like retaining means having a flat circular cross section base and a tubular shaped wall section having on the outside wall at its upper end a threaded portion, and said top component comprising a circular cross section top means having a flat circular cross section top and a tubular shaped hollow wall section connected at its top end to said top, said wall section having on the inside wall at its lower end a threaded portion for mating engagement with said threaded portion of said bottom component, said flat top having attached at a central point to the uppermost surface an attachment means in the form of an open or closed loop, wherein said bottom component has three circular cross section flow through apertures from the bottom surface of the base to the uppermost surface of said component which are spaced equidistant apart on a circular cross section and has three circular cross section sample bottle holding apertures to receive volatiles analysis glass sample bottles said apertures being from the uppermost surface of said component to the bottom surface of said component and being of sufficient diameter to receive said volatiles analysis glass sample bottles from the uppermost surface of said component to a point about 0.1 to about 0.3 cm above the bottom surface of said component and being of a lesser diameter of about one half to three quarters of the aforesaid diameter to the bottom surface of said component and being spaced equidistant apart on a circular cross section and being located about equidistant apart from said flow through apertures, and wherein said flat top of said top component has three circular cross section flow in apertures being about the diameter of the sample bottle holding apertures in the bottom surface of said bottom component and being spaced equidistant apart on a circular cross section of essentially identical radius as said sample bottle holding apertures of said bottom component, and wherein the height of said wall section of said top component is such that when matingly engaged with the bottom component at the threaded portions, said volatiles analysis glass sample bottles are loosely retained in said sample bottle holding apertures such that the water to be sampled flows about and into said sample bottles and excess water flows out of said sampling unit.

Further, according to my invention there is provided a method of obtaining water samples for subsequent analysis wherein the aforesaid sampling unit, equipped with three volatiles analysis glass sample bottles, is immersed in the water stream to be sampled for sufficient time to fill the sampling unit with water, the sampling unit is removed from the water stream and excess water is allowed to drain away, the top component of said sampling unit is removed, and the three sample bottles are removed from the bottom component, the water contained in one of said sample bottles is transferred to each of the remaining two sample bottles to provide two filled sample bottles having a reverse meniscus formed on the water at the top of each sample bottle and a bottle cap comprising a septum and a cap closure is affixed to the top of the two filled sample bottles.

BRIEF DESCRIPTION OF THE DRAWINGS

FIG. 3 is a schematic drawing of the sampling unit.

FIG. 4 is a drawing of the cross-section AA of FIG. 2.

DETAILED DESCRIPTION AND PREFERRED EMBODIMENTS

The containment unit of my invention is metal, preferably stainless steel and most preferably stainless steel finished to a smooth surface. This construction and finish meets government set regulations and also is durable and generally corrosion resistant. The volatiles analysis glass sample bottles are well known in the art and are generally of a size to hold about 25 ml or about 40 ml of liquid and are equipped with a detachable screw on bottle cap comprising a septum and a cap closure. The septum is preferably a butyl rubber layer protected on the outside with a teflon layer, suitable for penetration with a syringe needle for sample removal. The cap closure preferably contains the septum within it and is a plastic screw-on type which can be screwed on tightly onto the top of the sample bottles.

The containment unit is sized so as to contain within it the sample bottles. I prefer to use the 40 ml sample bottles and have sized the containment unit accordingly. The attachment means attached to the uppermost side of the flat top of the top component may be an open or closed loop and preferably is a closed loop stainless steel unit welded to the top. By this means a chain or other long device having a hook or shackle on its end may be attached to the sampling unit allowing it to be lowered into and raised from the water stream to be sampled. As a result of the sampling unit being of a cylindrical form it can also be lowered through access pipes of suitable diameter into an otherwise inaccessible water stream.

Figure 1:
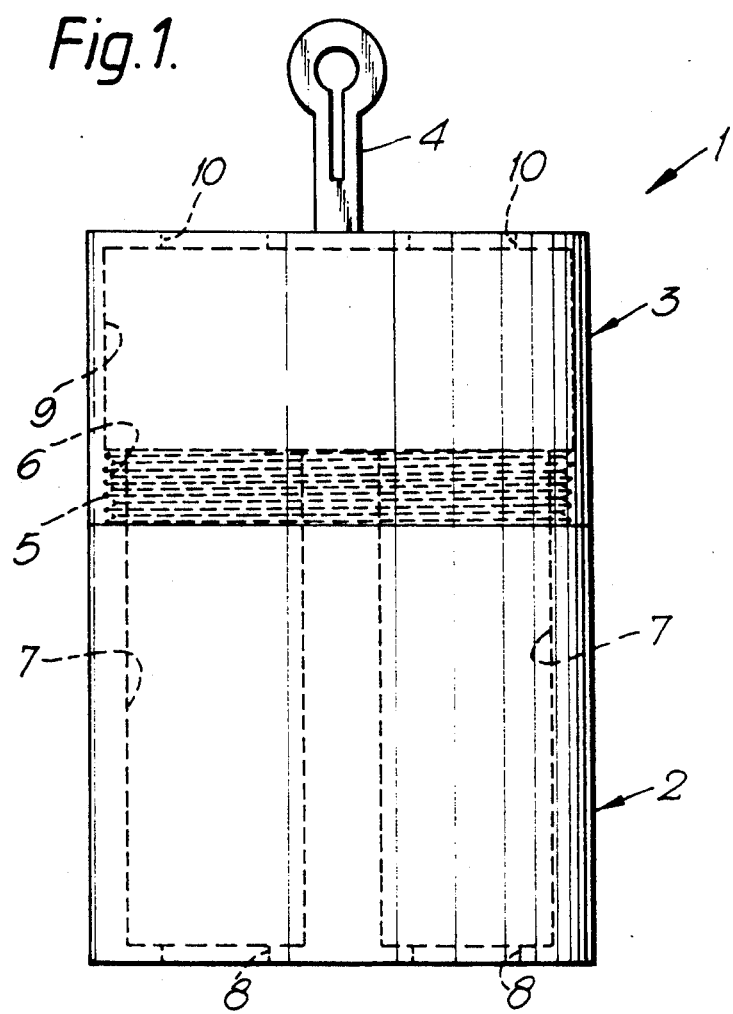
FIG. 1 is a schematic drawing of the containment unit.
Figure 2:
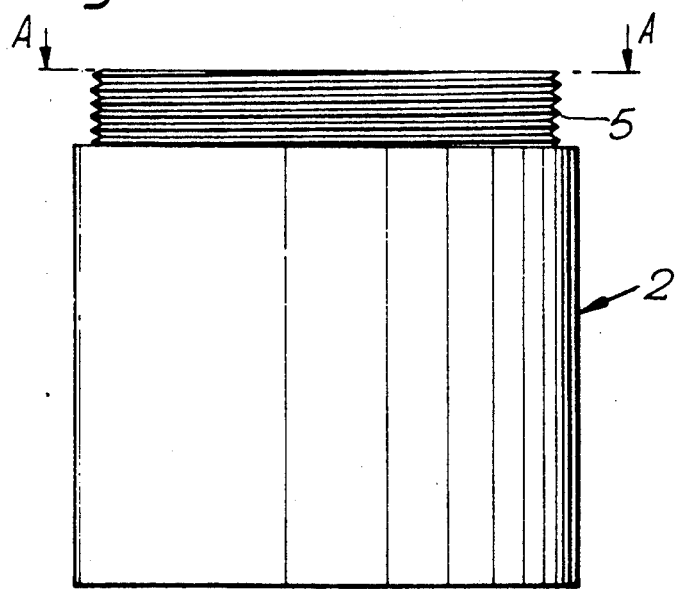
FIG. 2 is a schematic outline of the bottom component.

A preferred embodiment of the sampling unit which utilizes the 40 ml sample bottles is now described with reference to the Figures which are schematic drawings of a sampling unit. In FIG. 1, the sampling unit 1 comprises a bottom component 2 and a top component 3. The bottom component 2 has a threaded portion 5 at its upper end and has three (only two shown) circular cross section sample bottle holding apertures 7 having lesser diameter apertures 8 toward the bottom surface of the bottom component. The top component 3 has a tubular shaped hollow wall section 9, has a threaded portion 6 for mating engagement with the threaded portion 5 of the bottom component, has an attachment means 4 in the form of a closed loop attached to the uppermost surface and has three (only two shown) circular cross section flow in apertures 10 which are about the diameter of the sample bottle holding apertures on the bottom surface of the bottom components 8. FIG. 2 is a simple drawing of the bottom component 2 showing the threaded portion 5. FIG. 3 is essentially the same as FIG. 1 except that the volatiles analysis glass sample bottles 11 are shown. FIG. 4 is the cross section AA of FIG. 2 and shows the bottom component 2, the threaded portion 5, the circular cross section sample bottle holding apertures 7 and the lesser diameter apertures 8 and further shows the circular cross section flow through apertures 12. As can be seen in FIG. 4, the sample bottle holding apertures 7 are spaced equidistant apart on a circular cross section, the flow through apertures 12 are spaced equidistant apart on a circular cross section and the bottle holding apertures 7 are located about equidistant apart from the flow through apertures 12. Most preferably the centre points of the sample holding apertures are on a circle of lesser radius than the radius of the circle on which the centre points of the flow through apertures are located.

In the method of using the sampling unit to obtain water samples, the top component is unscrewed and removed from the bottom component, the three volatiles analysis sample bottles are inserted into their locations in the bottom component, the top component is screwed back onto the bottom component,, a suitable chain or line is attached to the attachment means and the sampling unit is lowered into the water stream to complete immersion for about 10 to 20 seconds and then raised from the water stream. When excess residual water has drained from the unit, the top component is unscrewed and removed from the bottom component. Two of the sample bottles are removed and the water in one of these is transferred to the other sample bottle to provide a filled sample bottle having a reverse meniscus formed on the water at the top of the sample bottle following which a bottle cap, comprising a septum and a cap closure, is affixed to the top of the filled sample bottle. The third sample bottle is removed and water from the previously used bottle is used to provide a second filled sample bottle having a reverse meniscus formed on the water at the top of the sample bottle following which a bottle cap is affixed to the filled sample bottle. Thus, duplicate samples of the water stream are provided in containers which contain no air and are available for use for such analytical procedures as are desired, the second sample usually being retained for repeat or recheck analyses.

EXAMPLE

A sampling unit was constructed in accordance with the invention. The bottom and top components were stainless steel about 7.7 cm diameter and were finished to a smooth surface finish. The bottom component had a total height of about 6.8 cm, the threaded portion occupying about 1 cm of the upper portion. The three flow through apertures were about 1.3 cm diameter and were located such that their centres were 120° apart on an about 2.5 cm radius from the centre of the component. The three sample bottle holding apertures were about 2.8 cm diameter with a diameter of about 1.5 cm for the about 0.2 cm closest to the bottom surface and were located such that their centres were 120° apart on an about 1.9 cm radius from the centre of the component. The centre of any one sample bottle holding aperture was 60° apart from the centre of the two adjacent flow through apertures. The top component had a total height of about 5.3 cm, the top being about 0.6 cm thick and the wall section being about 0.5 cm thick, the threaded portion on the inside wall occupying about 1 cm of the lower inner wall. At the centre of the top surface of the top component was welded on a closed loop attachment of about 5 cm length. The three flow in apertures were about 1.6 cm diameter and were located such that their centres were 120° apart on an about 1.9 cm radius from the centre of the component.

The volatiles analysis glass sample bottles are commercially available, hold about 40 ml of liquid and have a screw top to the external walls. The sample bottles were dried at elevated temperature, cooled and the bottle caps applied. Immediately prior to use, the bottle caps are removed, the bottles placed in the bottom component of the sampling unit, the top component was screwed into place, a 10 m chain was attached to the attachment means of the top component, the whole was lowered through a 15 cm vertical pipe into an approximately 165 cm diameter water outlet pipe at a depth of about 8 m, the sampling unit was left in the water stream for about fifteen seconds and then withdrawn. After the excess water had drained away, the top component was unscrewed and removed. Two sample bottles were removed from the bottom component and one was used to completely fill the other bottle until a reverse meniscus had formed on the top following which the bottle cap was screw on. The third sample bottle was removed from bottom component and was likewise topped up with water to form a reverse meniscus following which the bottle cap was screwed on. These two capped bottles were suitably labelled as duplicate samples for analysis. The water left in the remaining bottle was discarded.

Similar use of the sampling unit was made to obtain duplicate samples from various water streams through the plant site, both below ground and at ground level.

What is claimed is:

1. A sampling unit for collecting water samples for subsequent analysis, wherein said sampling unit comprises a metal containment unit and contained within said containment unit three volatiles analysis glass sample bottles, wherein said containment unit comprises a bottom component and a top component, said bottom component comprising a circular cross section rod-like retaining means having a flat circular cross section base and a tubular shaped wall section having on the outside wall at its upper end a threaded portion, and said top component comprising a circular cross section top means having a flat circular cross section top and a tubular shaped hollow wall section connected at its top end to said top means, said wall section having on the inside wall at its lower end a threaded portion for mating engagement with said threaded portion of said bottom component, said flat top having attached at a central point to the uppermost surface an attachment means in the form of an open or closed loop, wherein said bottom component has three circular cross section flow through apertures from the bottom surface of the circular cross section base to the uppermost surface of said bottom component which are spaced equidistant apart on a circular cross section and has three circular cross section sample bottle holding apertures to receive volatiles analysis glass sample bottles, said sample bottle holding apertures being from the uppermost surface of said bottom component to the bottom surface of said bottom component and being of sufficient diameter to receive said volatiles analysis glass sample bottles from the uppermost surface of said bottom component to a point about 0.1 to about 0.3 cm above the bottom surface of said top component and being of a lesser diameter of about one half to three quarters of the aforesaid diameter to the bottom surface of said component and being spaced equidistant apart on a circular cross section and being located about equidistant apart from said flow through apertures, and wherein said flat top of said top component has three circular cross section flow in apertures being about the diameter of the sample bottle holding apertures in the bottom surface of said bottom component and being spaced equidistant apart on a circular cross section of essentially identical radius as said sample bottle holding apertures of said bottom component, and wherein the height of said wall section of said top component is such that when matingly engaged with the bottom component at the threaded portions, said volatiles analysis glass sample bottles are loosely retained in said sample bottle holding apertures such that the water to be sampled flows about and into said sample bottles and excess water flows out of said sampling unit.

2. The sampling unit of claim 1 wherein the metal is stainless steel and all surfaces are finished to a smooth surface.

3. The sampling unit of claim 1 wherein the volatiles analysis glass sample bottles hold about 40 ml of liquid.

4. A method of obtaining water samples from a water stream for subsequent analysis using the sampling unit of claim 1 wherein said sampling unit, equipped with three volatiles analysis glass sample bottles, is immersed in the water stream to be sampled for sufficient time to fill the sampling unit with water, the sampling unit is removed from the water stream and excess water is allowed to drain away, the top component of said sampling unit is removed and the three sample bottles are removed from the bottom component, the water contained in one of said sample bottles is transferred to each of the remaining two sample bottles to provide two filled sample bottles having a reverse meniscus formed on the water at the top of each sample bottle and a bottle cap comprising a septum and a cap closure is affixed to the top of the two filled sample bottles.

* * * * *